United States Patent
Lee et al.

(10) Patent No.: US 10,919,007 B2
(45) Date of Patent: Feb. 16, 2021

(54) ORGANIC MATERIAL PURIFICATION COMPOSITION AND METHOD OF PURIFYING ORGANIC MATERIALS USING THE SAME

(71) Applicants: SAMSUNG DISPLAY CO., LTD., Yongin-si (KR); DMS CO., LTD., Yongin-si (KR)

(72) Inventors: Myung-ki Lee, Seoul (KR); Hyunsoo Moon, Cheonan-si (KR); Jongwon Lee, Seongnam-si (KR); Sunwoo Kang, Hwaseong-si (KR); Yongseok Park, Seoul (KR)

(73) Assignees: Samsung Display Co., Ltd., Yongin-si (KR); DMS Co., Ltd., Yongin-si (KR)

( * ) Notice: Subject to any disclaimer, the term of this patent is extended or adjusted under 35 U.S.C. 154(b) by 205 days.

(21) Appl. No.: 16/144,302

(22) Filed: Sep. 27, 2018

(65) Prior Publication Data

US 2019/0091637 A1 Mar. 28, 2019

(30) Foreign Application Priority Data

Sep. 28, 2017 (KR) .......................... 10-2017-0126168

(51) Int. Cl.

| | | |
|---|---|---|
| *B01D 11/04* | (2006.01) | |
| *A61K 39/02* | (2006.01) | |
| *F01N 3/20* | (2006.01) | |
| *G05B 1/00* | (2006.01) | |
| *B01F 3/22* | (2006.01) | |
| *C07D 403/04* | (2006.01) | |
| *H01L 51/00* | (2006.01) | |
| *C07D 401/14* | (2006.01) | |
| *B01F 3/12* | (2006.01) | |
| *H01G 9/20* | (2006.01) | |

(52) U.S. Cl.
CPC .......... *B01F 3/2261* (2013.01); *B01F 3/1214* (2013.01); *B01F 3/223* (2013.01); *C07D 401/14* (2013.01); *C07D 403/04* (2013.01); *H01L 51/0025* (2013.01); *H01L 51/0067* (2013.01); *B01F 2003/125* (2013.01); *H01G 9/2013* (2013.01); *H01L 51/0072* (2013.01); *H01L 51/0077* (2013.01)

(58) Field of Classification Search
CPC ............. H01L 51/0025; H01L 51/0072; H01L 51/0077; H01L 51/0067; C07D 401/14; C07D 403/04; H01G 9/2013; B01F 3/1214; B01F 3/223; B01F 3/2261; B01F 2003/125
USPC ......................................... 422/255, 243, 105
See application file for complete search history.

(56) References Cited

U.S. PATENT DOCUMENTS

| | | | |
|---|---|---|---|
| 8,754,254 B2 * | 6/2014 | Bhattacharyya | ........ C07C 51/43 562/485 |
| 2009/0253924 A1 * | 10/2009 | Lim | ........ C07C 57/08 554/103 |
| 2013/0219949 A1 | 8/2013 | Seiler et al. | |

FOREIGN PATENT DOCUMENTS

| | | | |
|---|---|---|---|
| JP | 2015-189679 A | 11/2015 | |
| KR | 10-0845687 B1 | 7/2008 | |
| KR | 10-1233447 B1 | 2/2013 | |
| KR | 10-1404833 B1 | 5/2014 | |
| KR | 10-1470114 B1 | 12/2014 | |
| KR | 10-1483845 B1 | 1/2015 | |
| KR | 10-1542344 B1 | 7/2015 | |
| KR | 10-1539991 B1 | 8/2015 | |
| KR | 10-2016-0145971 A | 12/2016 | |
| KR | 10-1743510 B1 | 5/2017 | |
| WO | WO-2015147487 A1 * | 10/2015 | ........... C07C 209/84 |

OTHER PUBLICATIONS

Park, WO 2015147487 Machine Translation, Oct. 1, 2015 (Year: 2015).*

* cited by examiner

*Primary Examiner* — Jessica Whiteley
(74) *Attorney, Agent, or Firm* — Lewis Roca Rothgerber Christie LLP

(57) ABSTRACT

An organic material purification composition, a mixed composition, and a method of purifying an organic material, the organic material purification composition including an ionic liquid in which a cation and an anion are combined; and an organic solvent, wherein the organic solvent includes an alcohol or a ketone.

24 Claims, 3 Drawing Sheets

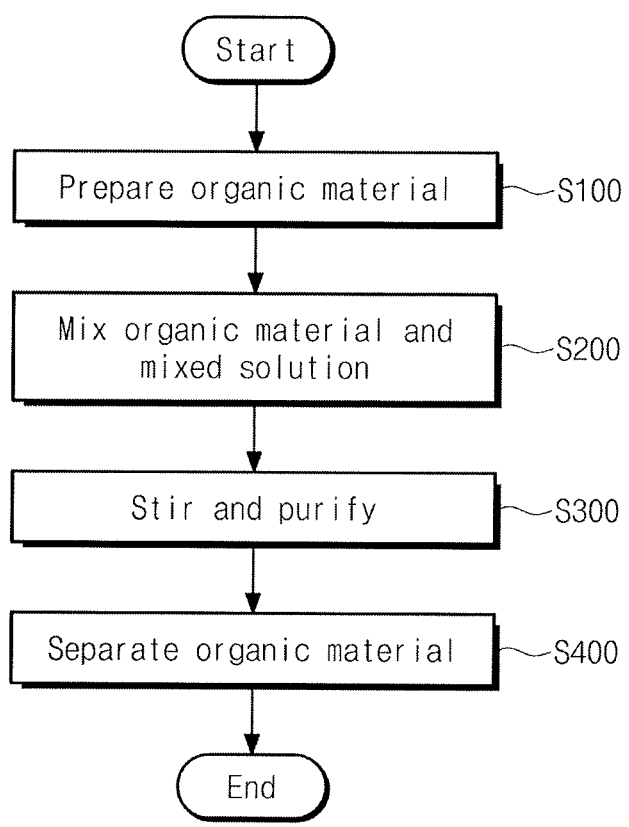

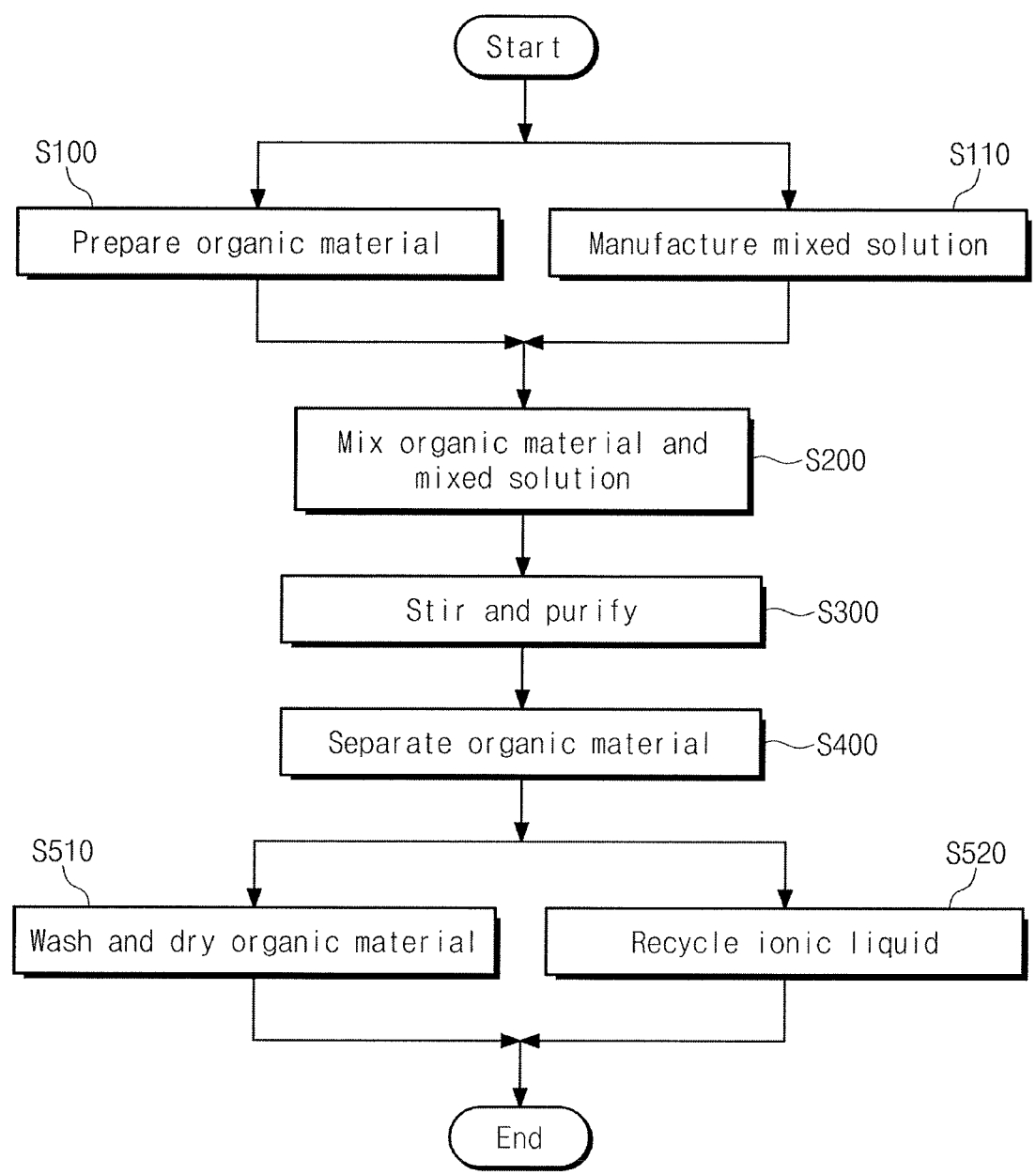

ORGANIC MATERIAL PURIFICATION COMPOSITION AND METHOD OF PURIFYING ORGANIC MATERIALS USING THE SAME

CROSS-REFERENCE TO RELATED APPLICATION

Korean Patent Application No. 10-2017-0126168, filed on Sep. 28, 2017, in the Korean Intellectual Property Office, and entitled: "Organic Material Purification Composition and Method of Purifying Organic Materials Using the Same," is incorporated by reference herein in its entirety.

BACKGROUND

1. Field

Embodiments relate to an organic material purification composition and a method of purifying organic materials using the same.

2. Description of the Related Art

As an image display device, an organic light emitting display (LED) device has been actively developed. An organic light emitting display device is different from a liquid crystal display device, and the like in that it is a self-luminescence display device that realizes display by recombining holes and electrons injected from a first electrode and a second electrode in a light emitting layer to emit a light emitting material which is an organic compound included in the light emitting layer.

An organic light emitting device may include, e.g., a first electrode, a hole injection layer disposed on the first electrode, a hole transport layer disposed on the hole injection layer, a light emitting layer disposed on the hole transport layer, an electron transport layer disposed on the light emitting layer, an electron injection layer disposed on the electron transport layer, and a second electrode disposed on the electron injection layer.

SUMMARY

Embodiments are directed to an organic material purification composition and a method of purifying organic materials using the same.

The embodiments may be realized by providing an organic material purification composition including an ionic liquid in which a cation and an anion are combined; and an organic solvent, wherein the organic solvent includes an alcohol or a ketone.

The alcohol may include methanol, ethanol, propanol, or butanol, and the ketone may include acetone.

The cation of the ionic liquid may be represented by one of Formulae 1-1 to 1-7 below:

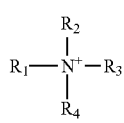

[Formula 1-1]

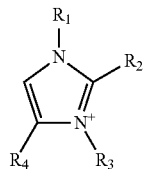

[Formula 1-2]

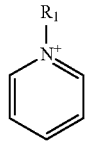

[Formula 1-3]

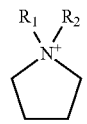

[Formula 1-4]

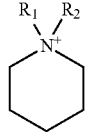

[Formula 1-5]

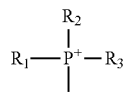

[Formula 1-6]

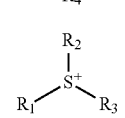

[Formula 1-7]

wherein, in Formulae 1-1 to 1-7, $R_1$ to $R_4$ may each independently be a substituted or unsubstituted alkyl group having 2 to 20 carbon atoms.

One of $R_1$ to $R_4$ may be an alkyl group having a straight chain of 12 to 20 carbon atoms.

The anion of the ionic liquid may include $Cl^-$, $Br^-$, $NO_3^-$, $BF_4^-$, $PF_6^-$, $AlCl_4^-$, $Al_2Cl_7^-$, $AcO^-$, $CH_3COO^-$, $CF_3COO^-$, $CH_3SO_3^-$, $CF_3SO_3^-$, $(CF_3SO_2)_2N^-$, $(CF_3SO_2)_3C^-$, $(CF_3CF_2SO_2)_2N^-$, $C_4F_9SO_3^-$, $C_3F_7COO^-$, $(CF_3SO_2)(CF_3CO)N^-$, $C_4F_{10}N^-$, $C_2F_6NO_4S_2^-$, $C_2F_6NO_6S^-$, $C_4F_{10}NO_4S_2^-$, $CF_3SO_2^-$, $CF_3SO_3^-$, $C_4F_9SO_2^-$, $C_4F_9SO_3^-$, $C_2H_6NO_4S_2^-$, $C_3F_6NO_3S^-$, $(CF_3SO_2)_2N^-$, $CH_3CH(OH)CO_2^-$, or a combination thereof.

A weight ratio of the organic solvent to the ionic liquid may be from 1.0 to 5.0.

The organic material purification composition may be configured to purify an organic material for a light emitting layer of an organic light emitting device.

The embodiments may be realized by providing a mixed composition including an ionic liquid in which a cation and an anion are combined; and an organic solvent, wherein the organic solvent includes an alcohol or a ketone, and wherein a weight ratio of the organic solvent to the ionic liquid is from 1.0 to 5.0.

The composition may include 16 wt % to 50 wt % of the ionic liquid; and a balance of the organic solvent.

The mixed composition may have a viscosity of 15 cP or less at 20° C. to 25° C.

The alcohol may include methanol, ethanol, propanol, or butanol, and the ketone may include acetone.

The embodiments may be realized by providing a method of purifying an organic material, the method including preparing an organic material to be purified; mixing the organic material with a mixed solution of an ionic liquid and an organic solvent, the organic solvent including an alcohol or a ketone; purifying the organic material by stirring the mixed solution in which the organic material is mixed; and separating the purified organic material.

The ionic liquid may include a cation represented by one of Formulae 1-1 to 1-7 below:

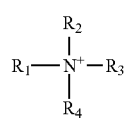

[Formula 1-1]

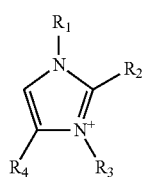

[Formula 1-2]

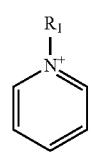

[Formula 1-3]

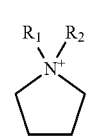

[Formula 1-4]

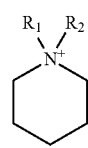

[Formula 1-5]

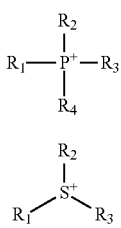

[Formula 1-6]

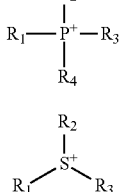

[Formula 1-7]

wherein, in Formulae 1-1 to 1-7, $R_1$ to $R_4$ may each independently be a substituted or unsubstituted alkyl group having 2 to 20 carbon atoms.

The ionic liquid may include an anion, the anion including $Cl^-$, $Br^-$, $NO_3^-$, $BF_4^-$, $PF_6^-$, $AlCl_4^-$, $Al_2Cl_7^-$, $AcO^-$, $CH_3COO^-$, $CF_3COO^-$, $CH_3SO_3^-$, $CF_3SO_3^-$, $(CF_3SO_2)_2N^-$, $(CF_3SO_2)_3C^-$, $(CF_3CF_2SO_2)_2N^-$, $C_4F_9SO_3^-$, $C_3F_7COO^-$, $(CF_3SO_2)(CF_3CO)N^-$, $C_4F_{10}N^-$, $C_2F_6NO_4S_2^-$, $C_2F_6NO_6S_2^-$, $C_4F_{10}NO_4S_2^-$, $CF_3SO_2^-$, $CF_3SO_3^-$, $C_4F_9SO_2^-$, $C_4F_9SO_3^-$, $C_2H_6NO_4S_2^-$, $C_3F_6NO_3S^-$, $(CF_3SO_2)_2N^-$, $CH_3CH(OH)CO_2^-$, or a combination thereof.

The alcohol may include methanol, ethanol, propanol, or butanol, and the ketone may include acetone.

The mixed solution of the ionic liquid and the organic solvent may include 16 wt % to 50 wt % of the ionic liquid; and a balance of the organic solvent.

The organic material may be a conductive organic material for a light emitting layer of an organic light emitting device.

The organic material may include a first organic material having a first polarity; and a second organic material having a second polarity that is different from the first polarity.

During purifying the organic material by stirring the mixed solution in which the organic material is mixed, the first organic material may be dissolved in the mixed solution, and the second organic material may not be dissolved in the mixed solution.

Separating the purified organic material may include separating the second organic material through a filter.

Mixing the organic material with the mixed solution and purifying the organic material by stirring the mixed solution in which the organic material is mixed may be performed at 20° C. to 25° C.

The method may further include washing and drying the separated organic material after separating the purified organic material.

The method may further include purifying and recycling the ionic liquid in the mixed solution from which the organic material is separated after separating the purified organic material.

The method may further include preparing the mixed solution by mixing and then stirring the organic solvent and the ionic liquid prior to mixing the organic material with the mixed solution.

BRIEF DESCRIPTION OF THE DRAWINGS

Features will be apparent to those of skill in the art by describing in detail exemplary embodiments with reference to the attached drawings in which:

FIG. 2 illustrates a flowchart of an organic material purification method according to an embodiment;

FIG. 3 illustrates a flowchart of an organic material purification method according to an embodiment.

DETAILED DESCRIPTION

Figure 1:
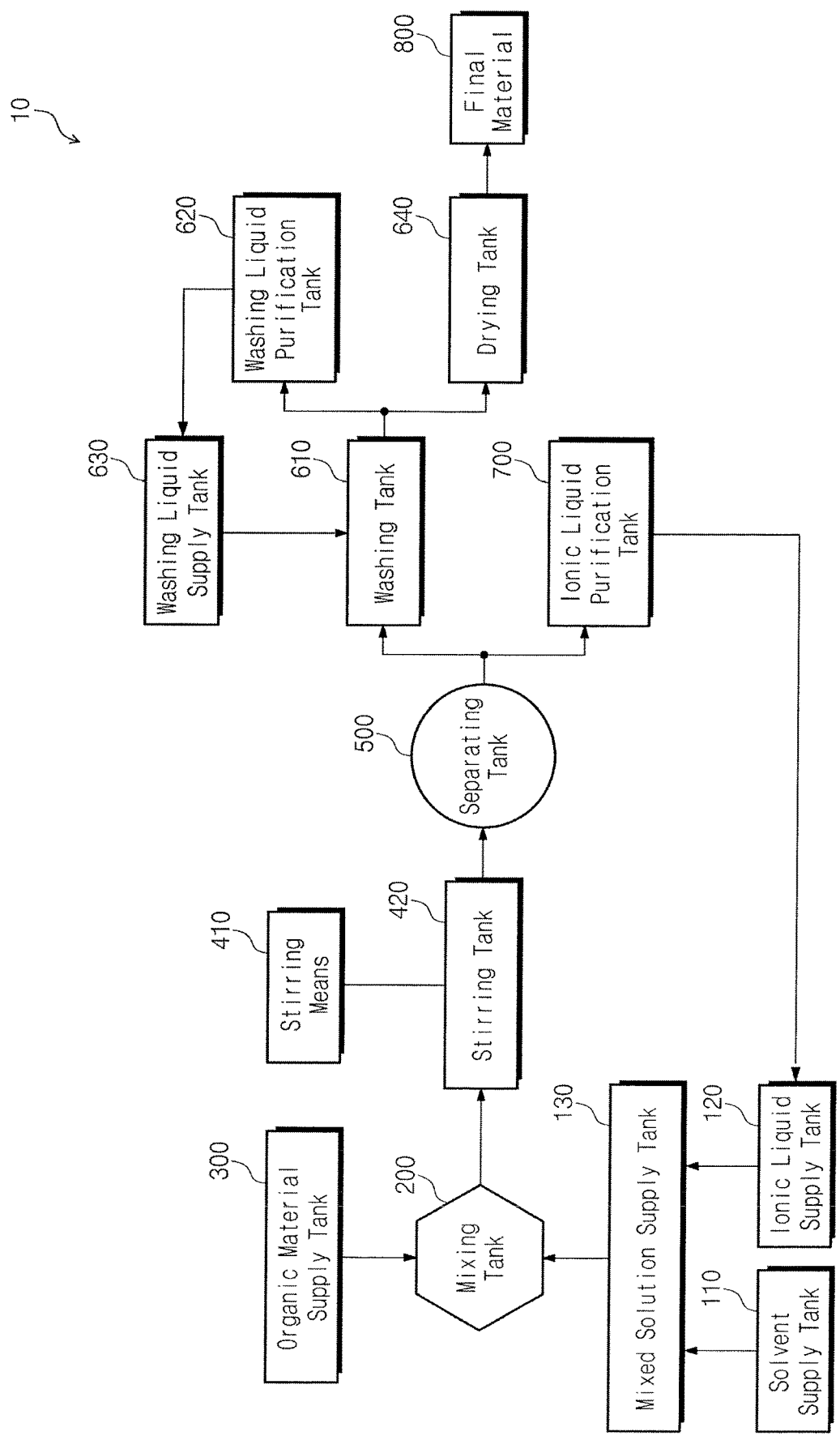
FIG. 1 illustrates a block diagram schematically showing an organic material purification apparatus used in an organic material purification method according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. In addition, it will also be understood that when a layer is referred to as being "between" two layers, it can be the only layer between the two layers, or one or more intervening layers may also be present.

In describing each drawing, similar reference numerals were used for similar elements. It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. The terms of a singular form may include plural forms unless the context clearly indicates otherwise. As used herein, the term "or" is not an exclusive term, and has the same meaning as "and/or".

In this application, terms like "include," "comprise," or "have" are intended to designate features, numbers, steps, operations, elements, parts, or combinations thereof described in the specification but not to exclude the possibility of the presence or the addition of one or more other features, numbers, steps, operations, elements, parts, or combinations thereof. It will also be understood that when a portion, such as a layer, a film, a region, and a plate is referred to as being "on" another portion, it can be "directly on" the other portion, or one or more intervening portions may also be present. On the other hand, it will be understood that when a portion, such as a layer, a film, a region, and a plate is referred to as being "under" another portion, it can be "directly under", or one or more intervening portions may also be present.

Hereinafter, a mixed composition according to an embodiment will be described.

A mixed composition according to an embodiment may be a composition for purifying organic materials. In an implementation, the mixed composition may be a composition for purifying organic materials included in an organic light emitting device. Organic materials purified by the mixed composition may be included in any one of plurality of organic layers disposed between a positive electrode and a negative electrode of the organic light emitting device. For example, the mixed composition may be a composition for purifying organic materials included in a light emitting layer of the organic light emitting device. Hereinafter, for convenience of explanation, the mixed composition according to an embodiment will be referred to as an organic material purification composition.

The organic material purification composition according to an embodiment may include, e.g., an ionic liquid and an organic solvent.

In this specification, the ionic liquid refers to a liquid composed only of ions. The ionic liquid may be molten salt consisting of a cation having a larger volume and an anion having a smaller volume.

The cation of ionic liquid may include, e.g., ammonium, imidazolium, pyridinium, pyrrolidinium, phosphonium, sulfonium, or a combination thereof. In an implementation, the cation of the ionic liquid may be represented by, e.g., one of Formulae 1-1 to 1-7 below.

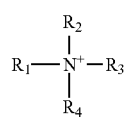

[Formula 1-1]

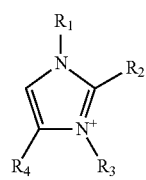

[Formula 1-2]

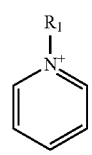

[Formula 1-3]

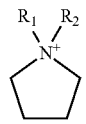

[Formula 1-4]

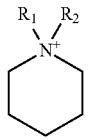

[Formula 1-5]

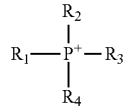

[Formula 1-6]

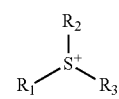

[Formula 1-7]

In Formulae 1-1 to 1-7, $R_1$ to $R_4$ may each independently be or include, e.g., a substituted or unsubstituted alkyl group having 2 to 20 carbon atoms. In an implementation, $R_1$ to $R_4$ may each independently be an alkyl group having a straight chain or a side or branched chain. In an implementation, one of $R_1$ to $R_4$ may be, e.g., an alkyl group having a straight chain of 12 carbon atoms or more (e.g., 12 to 20 carbon atoms). When one of $R_1$ to $R_4$ has a long straight chain of 12 carbon atoms or more, the ionic liquid may be in a liquid state having a relatively low viscosity even at room temperature (20° C. to 25° C.).

The anion of the ionic liquid may include, e.g., $Cl^-$, $Br^-$, $NO_3^-$, $BF_4^-$, $PF_6^-$, $AlCl_4^-$, $Al_2Cl_7^-$, $AcO^-$, $CH_3COO^-$, $CF_3COO^-$, $CH_3SO_3^-$, $CF_3SO_3^-$, $(CF_3SO_2)_2N^-$, $(CF_3SO_2)_3C^-$, $(CF_3CF_2SO_2)_2N^-$, $C_4F_9SO_3^-$, $C_3F_7COO^-$, $(CF_3SO_2)(CF_3CO)N^-$, $C_4F_{10}N^-$, $C_2F_6NO_4S_2^-$, $C_2F_6NO_6S_2^-$, $C_4F_{10}NO_4S_2^-$, $CF_3SO_2^-$, $CF_3SO_3^-$, $C_4F_9SO_2^-$, $C_4F_9SO_3^-$, $C_2H_6NO_4S_2^-$, $C_3F_6NO_3S^-$, $(CF_3SO_2)_2N^-$, $CH_3CH(OH)CO_2^-$, or a combination thereof.

The ionic liquid may be formed by various combinations of cations and anions depending on the characteristics of an organic material to be purified. For example, in the organic material purification composition according to an embodiment, the ionic liquid may include an imidazolium cation. In an implementation, the ionic liquid may include a bis (trifluoromethanesulfone)imide (TFSI) anion. In an implementation, the ionic liquid may be, e.g., represented by Formula 2 below.

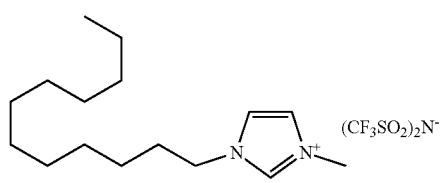

[Formula 2]

The ionic liquid has a structure of which a cation having a relatively larger volume and an anion having a relatively smaller volume are combined so as to have a low melting point and low vapor pressure, so that the ionic liquid may exist as a liquid stable in a wide range of temperatures. The ionic liquid may have high terminal stability and high ionic conductivity, and may be highly soluble in hydrophilic and hydrophobic organic, inorganic and polymeric materials. The ionic liquid may be used as a material for dissolving an organic material. In addition, the ionic liquid may have low volatility, low flame retardancy (e.g., may be flame retardant), and low explosiveness, so that the ionic liquid may be a more environmentally friendly material than conventional organic solvents.

In the organic material purification composition according to an embodiment, the ionic liquid may be a main dissolving material for purifying organic materials. For example, for an organic material mixture including a plurality of organic materials having different polarities from each other, the ionic liquid may separate and purify each of the organic materials through solubility differences among the plurality of organic materials.

In the organic material purification composition according to an embodiment, an organic solvent may adjust the viscosity of the organic material purification composition. In the organic material purification composition according to an embodiment, the organic solvent may be a solvent of the mixed composition.

In the organic material purification composition according to an embodiment, the organic solvent may have a weight greater than or equal to the weight of the ionic liquid. In the organic material purification composition according to an embodiment, a ratio of the weight of the organic solvent to the weight of the ionic liquid (e.g., the weight ratio) may be, e.g., from 1.0 to 5.0. In an implementation, the organic material purification composition may include, e.g., about 16 wt % to about 50 wt % of the ionic liquid, and the remainder or balance being the organic solvent. For example, the organic material purification composition according to an embodiment may be composed of the ionic liquid and the organic solvent having a weight greater than or equal to the weight of the ionic liquid.

In the organic material purification composition according to an embodiment, the organic solvent may include, e.g., an alcohol or a ketone. In an implementation, the ketone may include, e.g., acetone. The alcohol may include, e.g., an alkyl chain having 1 to 20 carbon atoms. In an implementation, the alcohol may include, e.g., methanol, ethanol, propanol, butanol, or a combination thereof. The propanol may be, e.g., n-propanol or isopropanol. In an implementation, the alcohol may include, e.g., ethanol.

The organic material purification composition according to an embodiment may include the organic solvent (e.g., alcohol or ketone), so that the organic material purification composition may have a low viscosity. The organic material purification composition according to an embodiment may include the ionic liquid having a high viscosity at room temperature, and may include the organic solvent having a low viscosity at room temperature, so that the organic material purification composition may have a viscosity of, e.g., about 15 cP or less. In this specification, room temperature or ambient temperature refers to a temperature of about 20° C. to about 25° C. The organic material purification composition according to an embodiment may include, e.g., about 16 wt % to about 50 wt % of the ionic liquid, and the remainder being the organic solvent, so that the organic material purification composition may have a low viscosity of, e.g., about 15 cP or less at ambient temperature. Maintaining the amount of the ionic liquid at 50 wt % or less may help prevent an increase in the viscosity of the organic material purification composition at room temperature, thereby ensuring that the purification of the organic material may be achieved. Also, after the purification process, it may be possible to recycle the ionic liquid having a sufficiently low viscosity. Maintaining the amount of the ionic liquid at 16 wt % or greater may help prevent a reduction in the purification efficiency of organic material, so that a sufficient purification thereof may be achieved.

Hereinafter, a method of purifying organic materials, the method according to an embodiment will be described.

FIG. 1 illustrates a block diagram schematically showing an organic material purification apparatus 10 used in an organic material purification method according to an embodiment. FIG. 2 illustrates a flowchart of an organic material purification method according to an embodiment. FIG. 3 illustrates a flowchart of an organic material purification method according to an embodiment. Hereinafter, referring to FIGS. 1 to 3, an organic material purification method according to an embodiment concept will be described.

Referring to FIGS. 1 to 2, an organic material purification method according to an embodiment may include, e.g., preparing an organic material to be purified S100, mixing the organic material with a mixed solution (of ionic liquid and organic solvent) S200, purifying the organic material by stirring the mixed solution in which the organic material is mixed S300, and separating the purified organic material S400. Referring to FIG. 3, the organic material purification method according to an embodiment may further include preparing the mixed solution by mixing the organic solvent and ionic liquid S110 before mixing the organic material and the mixed solution S200. Referring to FIG. 3, the organic material purification method according to an embodiment may further include, after separating the purified organic material S400, washing and drying the organic material S510, and purifying and recycling the ionic liquid from which the organic material is separated S520.

In the purification method, the organic material to be purified may be a conductive organic material. In an implementation, the organic material may be an amorphous organic material included in an organic layer of an organic light emitting device. The organic light emitting device may include a plurality of organic layers disposed between an anode and a cathode, and the organic material included in at least one layer of the plurality of organic layers may be purified through the organic material purification method according to an embodiment. For example, the plurality of organic layers may include a hole injection layer, a hole transport layer, a light emitting layer, an electron transport layer, an electron injection layer, and the like, and the organic material may be a material included in the light emitting layer. In an implementation, the organic material may be a mixture in which a host material and a dopant material are mixed, both of which are included in the light emitting layer.

The organic material may be a mixture in which a plurality of materials having different polarities from each other are mixed. In an implementation, the organic material may include a first organic material having a first polarity, and a second organic material having a second polarity different from the first polarity. The first polarity may have a value greater than that of the second polarity. The value of the first polarity may be greater than the value of the second polarity by about 2.0 D (debye). In an implementation, the first organic material may be a dopant material having a higher polarity than that of the second organic material, and the second organic material may be a host material having a relatively low polarity.

The step of preparing an organic material S100 may include a step of recovering a material not deposited on an organic light emitting device among organic materials used in manufacturing the organic light emitting device. An organic material supply tank 300 may be a deposition apparatus used in providing the organic light emitting device. In the process of providing the organic light emitting device, a plurality of organic layers may be provided by sequentially laminating an organic material on a substrate through a deposition process. In this case, in addition to the organic material deposited on the substrate, there is an organic material to be adhered to the inside of the deposition apparatus, and in the step of preparing an organic material S100, a step of recovering the organic material adhered to the inside of the deposition apparatus may be included. For example, the step of preparing an organic material S100 may be, in a step of depositing a light emitting layer of an organic light emitting device, a step of recovering a mixture of host material and dopant material, the mixture adhered to an inner surface of the deposition apparatus instead of being deposited on the organic light emitting device. The step of preparing an organic material S100 may include a step of grinding the organic material recovered for the purifying step thereafter.

The organic material purification method according to an embodiment may include the step of preparing the mixed solution S110 by being provided with the organic solvent (e.g., alcohol or ketone) from a solvent supply tank 110, and by being provided with the ionic liquid from an ionic liquid supply tank 120.

The mixed solution may be an organic material purification composition in which the above-mentioned ionic liquid and the organic solvent are mixed. In the step of preparing the mixed solution S110, the ionic liquid and the organic solvent may be put in the same chamber and stirred for a predetermined period of time to prepare the mixed solution. The step of preparing the mixed solution S110 may be performed at ambient temperature (e.g., 25° C.). The step of preparing the mixed solution S110 may include a step in which the ionic solution and the organic solution are put in the same chamber and stirred for about 5 minutes using a stirrer or the like, so that the ionic liquid and the organic solution are uniformly mixed.

In the organic material purification method according to an embodiment, by being provided with the organic material from the organic material supply tank 300, and by being provided with the mixed solution from a mixed solution supply tank 130, mixing of the organic material and the mixed solution S200 may be performed. The organic material and the mixed solution may be mixed in a mixing tank 200 and then moved to a stirring tank 420 such that the organic material mixed in the mixed solution may be purified through the stirring S300. In the stirring tank 420, the organic material and the mixed solution may be uniformly mixed using a stirring device 410 such as a stirrer.

In the organic material purification method according to an embodiment, the organic material dissolved in the mixed solution may be purified by going through the mixing step S200, and the stirring step S300. In an implementation, the organic material to be purified may be a mixture in which a plurality of materials having different polarities are mixed. For example, the organic material may include the first organic material having the first polarity, and the second organic material having the second polarity which is lower than the first polarity. In the mixing step S200 and the stirring step S300, only the first organic material having a relatively high polarity may be dissolved in the mixed solution. The second organic material, which may not be dissolved in the mixed solution, may be separated by a filter or the like in the separating step S400 thereafter.

The mixing step S200 and the stirring step S300 may be processing steps that are continuously performed. The mixing step S200 and the stirring step S300 may be performed at ambient temperature (e.g., 25° C.). The mixing step S200 and the stirring step S300 may be performed, through a continuous process, by stirring the solution mixed in the mixing tank 200 through the stirring device 410 in the stirring tank 420 for about 30 minutes.

In the organic material purification method according to an embodiment, after the organic material is purified by being mixed and stirred in the stirring tank 420, the mixed solution including the purified organic material may be moved to a separating tank 500, and then the purified organic material may be separated from the mixed solution S400.

In the separating tank 500, the mixed solution of ionic liquid and organic solvent, and the purified organic material may be separated through a pressure filter or the like. The purified organic material may mean the second organic material that is not dissolved in the mixed solution with respect to the first organic material and the second organic material, both of which have different polarities. The first organic material having a relatively high polarity may be dissolved in the mixed solution and passed through the pressure filter. The second organic material having a relatively low polarity may be filtered by the pressure filter and be recovered from the filter. The separating step S400 may be performed for about 10 minutes.

The organic material purification method according to an embodiment may further include the step of washing and drying the organic material S510, the organic material separated in the separating tank 500.

The organic material separated in the separating tank 500 may be moved to a washing tank 610 to be washed. In the washing tank 610, the mixed solution of ionic liquid and organic solvent and the like, a portion of which is included in the separated organic material, and other impurities may be washed. In the washing step, a washing liquid provided from a washing liquid input tank 630 may be used for washing. The washing step may be performed by mixing the organic material with the washing liquid, sonicating the mixture for about 1 minute, and then stirring the sonicated mixture for about 5 minutes. The washing liquid may include an alcohol or ketone, e.g., ethanol or acetone. After the washing step, the washing liquid may be recovered to a washing liquid purification tank 620 to be purified, and then moved again to the washing liquid input tank 630 to be recycled.

The washed organic material may be moved to a drying tank 640 to be dried. The organic material moved to the drying tank 640 may be dried for a first time under atmospheric pressure (e.g., primary drying), and then dried for a second time under vacuum (e.g., secondary drying). The drying may be performed at about 100° C. The primary drying step may be performed for about 30 minutes and the secondary drying step may be performed for about 60 minutes. The organic material may become the final purified organic material 800 by being dried.

The organic material purification method according to an embodiment may further include a step of separating and recycling the ionic liquid from the mixed solution of ionic liquid and organic solvent S520, the mixed solution having passed through the filter in the separating tank 500.

The mixed solution that has passed through the filter of the separating tank 500 may be moved to an ionic liquid purification tank 700 such that the process of purifying the ionic liquid may be performed. For example, the ionic liquid may be purified by separating the second organic material, of the organic materials, not filtered by the filter in the separating tank 500, and by evaporating the organic solvent included in the mixed solution. The purified ionic liquid may be recirculated to the ionic liquid supply tank 120 to be used again for the purification of the organic material.

An ionic liquid may be capable of adjusting the solubility of materials having different polarities through the structural characteristics thereof, and therefore, may be used in a method of purifying organic materials including a plurality of materials having different polarities. However, an ionic liquid may have a high viscosity at ambient temperature, and a high processing temperature could be required. Also, when an organic material to be purified is mixed at a high concentration with an ionic liquid having a high viscosity, the viscosity of the ionic liquid-organic material mixed solution could become excessively high, so that the stirring thereof may not be achieved. Accordingly, the organic material may not be dissolved in the ionic solution, so that the purification of the organic material may not be achieved.

In addition, some organic material purification methods using only an ionic liquid may follow a method in which a plurality of materials having different polarities are completely dissolved in the ionic liquid, and then recrystallized though a change in temperature or pressure. However, in this case, a change in temperature or pressure may be required, the processing time may be increased, an additional processing for changing processing conditions may be required, and the purification processing cost may be increased.

In the organic material purification method according to an embodiment, a mixed composition in which an organic solvent (e.g., an alcohol or ketone) is mixed with an ionic liquid is used as a purification composition for purifying organic materials. Accordingly, the viscosity of the purification composition may be lowered, so that the purification of organic materials may be performed even in an ambient temperature range. In addition, the viscosity of the purification composition may be low, even when an organic material to be purified is mixed at a high concentration, and the organic material may be dissolved, so that the purification of the organic material may be performed. In the organic material purification method according to an embodiment, the viscosity of the purification composition may be low, a high pressure filter may not be required in the separating step, and the organic material may be separated by a simple filter. In the organic material purification method according to an embodiment, the viscosity of the purification composition may be low, and the mixed solution of ionic liquid and organic solution may be easily recovered after the separating step, so that the ionic liquid may be recycled.

In addition, unlike an organic material purification method using only an ionic liquid, in a purification method using a mixed composition in which an organic solvent is mixed with an organic liquid, the purification of organic materials may be performed through a method in which, by using the solubility differences between two materials having different polarities, a material having a relatively high polarity is dissolved, and a material having a relatively low polarity is not dissolved. Through such a purification method, in the organic material purification method according to an embodiment, a change in temperature or pressure is not required in the step of purifying organic materials, so that the processing time and the processing cost may be reduced.

Hereinafter, an organic material purification composition and an organic material purification method will be described in detail with reference to examples.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

(Evaluation of the Preparation and Characteristics of Organic Material Purification Compositions)

Organic material purification compositions according to Examples 1 to 3, and an organic material purification composition according to Comparative Example 1 were prepared as shown in Table 1 below, and the viscosities thereof according to Examples 1 to 3 and Comparative Example 1 were measured and shown. In Table 1, the unit representing the content of each element is mg, and the unit representing the viscosity is cP. The viscosities represent values measured at 25° C.

TABLE 1

|  | Ionic liquid | Alcohol | Viscosity |
|---|---|---|---|
| Example 1 | 2,400 | 2,400 | 11.6 |
| Example 2 | 2,400 | 4,800 | 8.1 |
| Example 3 | 2,400 | 7,200 | 4.6 |
| Comparative Example 1 | 2,400 | — | 128.3 |

In Table 1, a compound represented by Formula 2 below was used as the ionic liquid, and ethanol was used as the alcohol.

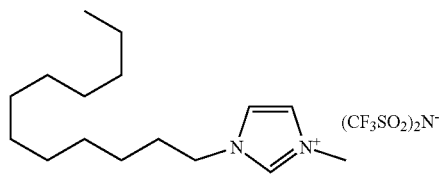

[Formula 2]

Referring to Table 1, an organic material purification composition including only an ionic liquid (as in Comparative Example 1) had a very high viscosity at ambient temperature due to the characteristics of the ionic liquid. However, in the Examples, by using a mixture of an ionic liquid and alcohol as an organic material purification composition, a purification composition having a low viscosity may be provided. For example, referring to Table 1, the organic material purification compositions according to Examples 1 to 3 had low viscosities of 15 cP or less by including the alcohol having a weight greater than or equal to that of the ionic liquid.

(Organic Material Purification Composition of Experimental Example 1—Evaluation of the Purification Performance of the Organic Material Purification Composition)

After performing a purification using organic material purification composition through an organic material purification method, the purification recovery rate and the purity of the purified material were evaluated.

In the Experimental Example, a compound represented by Formula 2, above, was used as the ionic liquid, and ethanol was used as the organic solvent. As a material to be purified, a material in which compounds represented by Formula 3 (a host material) and Formula 4 (a dopant material) below were mixed was used.

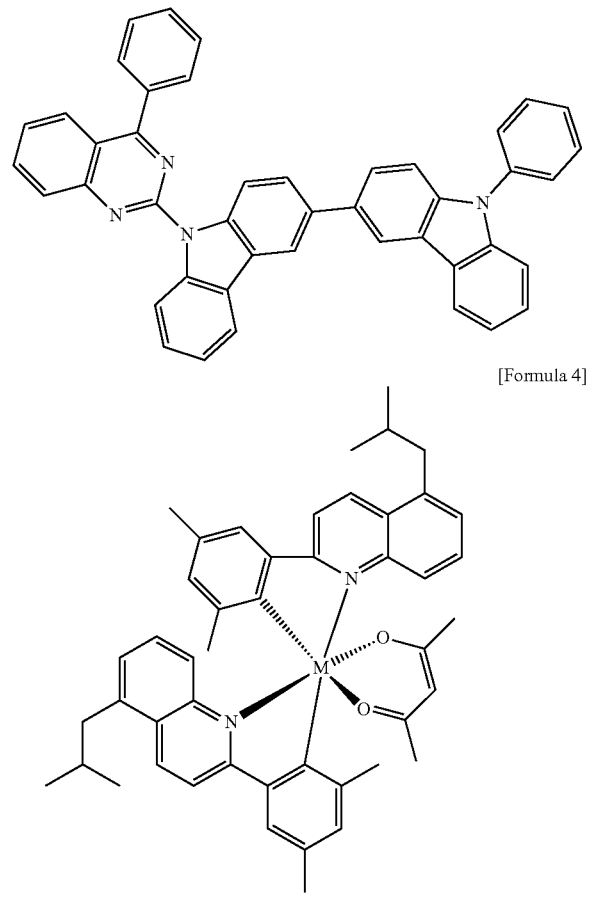

[Formula 3]

[Formula 4]

The purification of organic materials was performed on the mixed compositions of ionic liquid-alcohol having the contents described in Table 2, under the processing conditions described in Table 2. Specifically, the mixed compositions of ionic liquid-alcohol were mixed with the organic material to be purified and stirred for a predetermined period of time. The organic material not dissolved in the mixed composition was filtered through a pressure filter, and then washed and dried to recover the final purification compound. The mixing, stirring, filtering, and washing steps were performed at 25° C. As a separation filter, a filter having a gap of 0.5 m was used. The washing was performed by using ethanol as a washing solution. The drying was performed at 100° C. under atmospheric pressure for 30 minutes and dried under vacuum for 60 minutes.

In Table 2, time represents the time for which the organic material and the mixed compositions of ionic liquid-alcohol were mixed and stirred. In Table 2, purification recovery rate represents the ratio of the weight of the organic material after purification to the weight of the organic material before purification. In Table 2, material purity is a value obtained by measuring the concentration of the organic material represented by Formula 3 of the final purified compounds recovered after the purification process. In Table 2, the unit representing the contents of the organic material, ionic liquid, and alcohol is mg. The unit representing the time is minutes, and the unit representing the purification recovery rate and the material purity is %.

TABLE 2

| | Organic material | Ionic liquid | Alcohol | Time | Purification recovery rate | Material purity |
|---|---|---|---|---|---|---|
| Experimental Example 1 | 300 | 2,700 | 2,700 | 30 | 51 | 100 |
| Experimental Example 2 | 300 | 2,700 | 2,700 | 60 | 50 | 100 |
| Experimental Example 3 | 300 | 2,700 | 2,700 | 90 | 48 | 100 |
| Experimental Example 4 | 300 | 2,700 | 5,400 | 30 | 63 | 100 |
| Experimental Example 5 | 300 | 2,700 | 5,400 | 60 | 55 | 100 |
| Experimental Example 6 | 300 | 2,700 | 5,400 | 90 | 46 | 100 |
| Experimental Example 7 | 300 | 2,700 | 8,100 | 30 | 63 | 100 |
| Experimental Example 8 | 300 | 2,700 | 8,100 | 60 | 57 | 100 |
| Experimental Example 9 | 300 | 2,700 | 8,100 | 90 | 51 | 100 |
| Experimental Example 10 | 600 | 2,400 | 4,800 | 5 | 64 | 100 |
| Experimental Example 11 | 600 | 2,400 | 4,800 | 60 | 85 | 100 |
| Experimental Example 12 | 600 | 2,400 | 4,800 | 90 | 84 | 100 |
| Experimental Example 13 | 600 | 2,400 | 7,200 | 60 | 90 | 100 |
| Experimental Example 14 | 600 | 2,400 | 12,000 | 60 | 88 | 100 |
| Experimental Example 15 | 900 | 2,100 | 10,500 | 60 | 91 | 100 |
| Experimental Example 16 | 900 | 2,100 | 6,300 | 60 | 88 | 100 |
| Experimental Example 17 | 1,200 | 1,800 | 9,000 | 60 | 91 | 100 |

Referring to the results in Table 2, in the organic material purification method according to the Experimental Examples, it may be seen that an organic material may be separated at high purity even under a relatively low temperature condition. For example, in the organic material purification method according to the Experimental Examples, a mixed composition of ionic liquid-alcohol having a low viscosity was used, separation and purification were performed by using the solubility differences between two materials having different polarities, so that the two materials having different polarities may separated within a short stirring time of 90 minutes or less even under ambient temperature conditions (25° C.). For example, referring to the results of Experimental Examples 10 to 17 in Table 2, it may be that even when an organic material to be purified was mixed at a high concentration with the ionic liquid material, the material was purified at high purity at a high purification recovery rate.

In the organic material purification method according to the Experimental Examples, as a purification composition for purifying organic materials, a mixed composition in which alcohol is mixed with an ionic liquid was used. For example, a mixed composition that was mixed such that the weight ratio of the alcohol to the weight of the ionic liquid was 1:1 to 1:5 was used to perform the purification of the organic material. Accordingly, it may be seen that the viscosity of the purification composition was lowered, so that the purification of the organic material was achieved at ambient temperature. Also, it may be seen that the processing conditions such as temperature may not be changed throughout the entire process except in the drying step, and the processing time may be shortened to 90 minutes or less.

(Organic Material Purification Composition of Experimental Example 2—Evaluation of the Purification Performance of the Organic Material Purification Composition)

After performing the purification using the organic material purification composition through an organic material purification method, the purification recovery rate and the purity of the purified material were evaluated.

In the Experimental Examples, a compound represented by Formula 2, above, was used as an ionic liquid, and ethanol or acetone was used as a solvent. As a material to be purified, a mixed material in which GRH46, a host material, and GD976, a dopant material were mixed was used.

The purification of organic materials was performed using the mixed compositions of ionic liquid-organic solvent having the contents described in Table 3, under the processing conditions described in Table 3. Specifically, the mixed compositions of ionic liquid-organic solvent were mixed with the organic material to be purified and stirred for a predetermined period of time. The organic material not dissolved in the mixed composition was filtered through the pressure filter, and then washed and dried to recover the final purification compound. The mixing, stirring, filtering, and washing steps were performed at 25° C. As a separation filter, a filter having a gap of 0.5 μm was used. The washing was performed by using ethanol or acetone as a washing solution. The drying was performed at 100° C. under atmospheric pressure for 30 minutes and dried under vacuum for 60 minutes.

In Table 3, time represents the time for which the organic material and the mixed composition of ionic liquid-organic solvent were mixed and stirred. In Table 3, temperature represents the processing temperature at which the organic material and the mixed composition of ionic liquid-organic solvent were mixed and stirred. In Table 3, purification recovery rate represents the ratio of the weight of the organic material after purification to the weight of the organic material before purification. In Table 3, material purity is a value obtained by measuring the concentration of the host material of the final purified compounds recovered after the purification process. In Table 3, the unit representing the contents of the organic material, ionic liquid, and alcohol is mg. The unit representing the time is minutes, the unit representing the temperature is ° C., and the unit representing the purification recovery rate and the material purity is %.

TABLE 3

| | Organic material | Ionic liquid | Organic solvent | Type of organic solvent | Temperature | Time | Type of washing liquid | Purification recovery rate | Material purity |
|---|---|---|---|---|---|---|---|---|---|
| Experimental Example 18 | 1,000 | 2,000 | 5,000 | Ethanol | 25 | 30 | Ethanol | 73.80 | 100 |
| Experimental Example 19 | 1,000 | 9,000 | 27,000 | Ethanol | 25 | 30 | Ethanol | 89.20 | 100 |
| Experimental Example 20 | 1,000 | 9,000 | 27,000 | Ethanol | 25 | 360 | Ethanol | 82.00 | 100 |
| Experimental Example 21 | 1,000 | 9,000 | 27,000 | Acetone | 25 | 360 | Acetone | 39.90 | 100 |
| Experimental Example 22 | 1,000 | 9,000 | 27,000 | Acetone | 25 | 60 | Acetone | 38.70 | 100 |
| Experimental Example 23 | 1,000 | 2,000 | 5,000 | Acetone | 25 | 60 | Acetone | 47.90 | 100 |
| Experimental Example 24 | 1,000 | 2,000 | 5,000 | Acetone | 25 | 60 | Ethanol | 77.30 | 100 |
| Experimental Example 25 | 1,000 | 2,000 | 1,000 | Acetone | 25 | 60 | Ethanol | 94.00 | 100 |
| Experimental Example 26 | 1,000 | 2,000 | 2,000 | Acetone | 25 | 60 | Ethanol | 91.50 | 100 |
| Experimental Example 27 | 1,000 | 1,000 | 9,000 | Acetone | 25 | 60 | Ethanol | 87.70 | 100 |
| Experimental Example 28 | 1,000 | 1,000 | 1,000 | Acetone | 25 | 60 | Ethanol | 92.30 | 100 |
| Experimental Example 29 | 1,000 | 1,000 | 3,000 | Acetone | 25 | 60 | Ethanol | 94.10 | 100 |
| Experimental Example 30 | 1,000 | 1,000 | 5,000 | Acetone | 25 | 60 | Ethanol | 92.90 | 100 |
| Experimental Example 31 | 1,000 | 2,000 | 5,000 | Acetone | 25 | 30 | Ethanol | 73.80 | 100 |
| Comparative Experimental Example 1 | 1,000 | 9,000 | — | — | 25 | 1440 | Ethanol | 79.10 | 100 |
| Comparative Experimental Example 2 | 1,000 | 9,000 | — | — | 100 | 60 | Ethanol | 75.40 | 100 |

Referring to the results in Table 3, in the organic material purification method according to the Experimental Examples, it may be seen that an organic material may be separated at high purity even under a relatively low temperature condition. For example, in the organic material purification method according to the Experimental Examples, a mixed composition of ionic liquid-organic solvent having a low viscosity was used, separation and purification are performed using the solubility differences between two materials having different polarities, so that the two materials having different polarities are separated within a short stirring time of 360 minutes or less even under an ambient temperature condition (25° C.). For example, referring to the results of Comparative Experimental Examples 1 and 2, when the purification was performed using only the ionic liquid (which is not mixed with the organic solvent), a long processing time of 24 hours or more was required to achieve the separation and purification of a material to be purified to the Experimental Examples' level, or a high temperature of 100° C. or more was required.

Also, referring to the results of Experimental Examples 25 to 31, even when acetone was used, instead of ethanol, as the organic solvent in a process of separating a specific host material and a dopant material, the purification recovery rates were similar to or higher than those when ethanol was used.

In the organic material purification method according to the Experimental Examples, as a purification composition for purifying organic materials, a mixed composition in which an organic solvent such as ethanol or acetone is mixed with an ionic liquid was used. Accordingly, it may be seen that the viscosity of the purification composition was lowered, so that the purification of the organic material was achieved at ambient temperature. Also, it may be seen that the processing conditions such as temperature may not be changed throughout the entire process except in the drying step, and the processing time may be shortened to 90 minutes or less.

By way of summation and review, if impurities were to be included in a conductive organic material used in a layer of an organic light emitting device, the impurities could have a serious adverse effect on the performance of the organic light emitting device. Therefore, a process of purifying the conductive organic material may be such that the conductive organic material has high purity of 99% or more. A process of recovering and then purifying again an organic material included in each layer of an organic light emitting device may be considered.

The embodiments may provide an organic material purification composition that is capable of purifying organic materials used for an organic light emitting device.

The embodiments may provide an organic material purification composition which may be used for purifying organic materials under ambient temperature conditions.

The embodiments may provide an organic material purification composition having a low viscosity at ambient temperature even though an ionic liquid is included therein.

The embodiments may provide a method of purifying organic materials capable of purifying organic materials at high purity, and capable of reducing processing time and cost.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic material purification composition, comprising: an ionic liquid in which a cation and an anion are combined; and an organic solvent, wherein the organic solvent includes an alcohol or a ketone, wherein the alcohol includes ethanol, propanol, or butanol.

2. The organic material purification composition as claimed in claim 1, wherein: the ketone includes acetone.

3. The organic material purification composition as claimed in claim 1, wherein the cation of the ionic liquid is represented by one of Formulae 1-1 to 1-7 below:

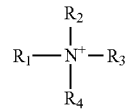

[Formula 1-1]

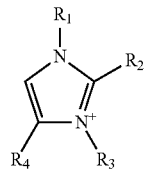

[Formula 1-2]

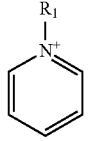

[Formula 1-3]

[Formula 1-4]

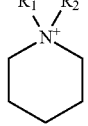

[Formula 1-5]

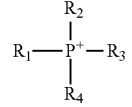

[Formula 1-6]

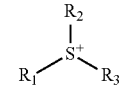

[Formula 1-7]

wherein, in Formulae 1-1 to 1-7, $R_1$ to $R_4$ are each independently a substituted or unsubstituted alkyl group having 2 to 20 carbon atoms.

4. The organic material purification composition as claimed in claim 3, wherein one of $R_1$ to $R_4$ is an alkyl group having a straight chain of 12 to 20 carbon atoms.

5. The organic material purification composition as claimed in claim 1, wherein the anion of the ionic liquid includes $Cl^-$, $Br^-$, $NO_3^-$, $BF_4^-$, $PF_6^-$, $AlCl_4^-$, $Al_2Cl_7^-$, $AcO^-$, $CH_3COO^-$, $CF_3COO^-$, $CH_3SO_3^-$, $CF_3SO_3^-$, $(CF_3SO_2)_2N^-$, $(CF_3SO_2)_3C^-$, $(CF_3CF_2SO_2)_2N^-$, $C_4F_9SO_3^-$, $C_3F_7COO^-$, $(CF_3SO_2)(CF_3CO)N^-$, $C_4F_{10}N^-$, $C_2F_6NO_4S_2^-$, $C_2F_6NO_6S_2^-$, $C_4F_{10}NO_4S_2^-$, $CF_3SO_2^-$, $CF_3SO_3^-$, $C_4F_9SO_2^-$, $C_4F_9SO_3^-$, $C_2H_6NO_4S_2^-$, $C_3F_6NO_3S^-$, $(CF_3SO_2)_2N^-$, $CH_3CH(OH)CO_2^-$, or a combination thereof.

6. The organic material purification composition as claimed in claim 1, wherein a weight ratio of the organic solvent to the ionic liquid is from 1.0 to 5.0.

7. The organic material purification composition as claimed in claim 1, wherein the organic material purification composition is configured to purify an organic material for a light emitting layer of an organic light emitting device.

8. A mixed composition, comprising: an ionic liquid in which a cation and an anion are combined; and an organic solvent, wherein the organic solvent includes an alcohol or a ketone, wherein the alcohol includes ethanol, propanol, or butanol, and wherein a weight ratio of the organic solvent to the ionic liquid is from 1.0 to 5.0.

9. The mixed composition as claimed in claim 8, wherein the composition includes: 16 wt % to 50 wt % of the ionic liquid; and a balance of the organic solvent.

10. The mixed composition as claimed in claim 8, wherein the mixed composition has a viscosity of 15 cP or less at 20° C. to 25° C.

11. The mixed composition as claimed in claim 8, wherein: the ketone includes acetone.

12. A method of purifying an organic material, the method comprising: preparing an organic material to be purified; mixing the organic material with a mixed solution of an ionic liquid and an organic solvent, the organic solvent including an alcohol or a ketone; purifying the organic material by stirring the mixed solution in which the organic material is mixed; and separating the purified organic material,
wherein the alcohol includes ethanol, propanol, or butanol.

13. The method as claimed in claim 12, wherein the ionic liquid includes a cation represented by one of Formulae 1-1 to 1-7 below:

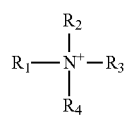

[Formula 1-1]

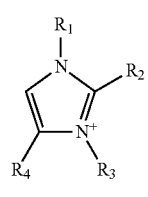

[Formula 1-2]

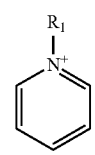

[Formula 1-3]

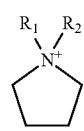

[Formula 1-4]

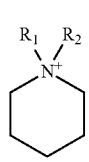

[Formula 1-5]

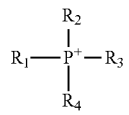

[Formula 1-6]

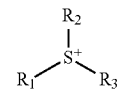

[Formula 1-7]

wherein, in Formulae 1-1 to 1-7, $R_1$ to $R_4$ are each independently a substituted or unsubstituted alkyl group having 2 to 20 carbon atoms.

14. The method as claimed in claim 12, wherein the ionic liquid includes an anion, the anion including $Cl^-$, $Br^-$, $NO_3^-$, $BF_4^-$, $PF_6^-$, $AlC_4^-$, $Al_2Cl_4^-$, $AcO^-$, $CH_3COO^-$, $CF_3COO^-$, $CH_3SO_3^-$, $CF_3SO_3^-$, $(CF_3SO_2)_2N^-$, $(CF_3SO_2)_3C^-$, $(CF_3CF_2SO_2)_2N^-$, $C_4F_9SO_3^-$, $C_3F_7COO^-$, $(CF_3SO_2)(CF_3CO)N^-$, $C_4F_{10}N^-$, $C_2F_6NO_4S_2^-$, $C_2F_6NO_6S_2^-$, $C_4F_{10}NO_4S_2^-$, $CF_3SO_2^-$, $CF_3SO_3^-$, $C_4F_9SO_2^-$, $C_4F_9SO_3^-$, $C_2H_6NO_4S_2^-$, $C_3F_6NO_3S^-$, $(CF_3SO_2)_2N^-$, $CH_3CH(OH)CO_2^-$, or a combination thereof.

15. The method as claimed in claim 12, wherein: the ketone includes acetone.

16. The method as claimed in claim 12, wherein the mixed solution of the ionic liquid and the organic solvent includes: 16 wt % to 50 wt % of the ionic liquid; and a balance of the organic solvent.

17. The method as claimed in claim 12, wherein the organic material is a conductive organic material for a light emitting layer of an organic light emitting device.

18. The method as claimed in claim 17, wherein the organic material includes: a first organic material having a first polarity; and a second organic material having a second polarity that is different from the first polarity.

19. The method as claimed in claim 18, wherein, during purifying the organic material by stirring the mixed solution in which the organic material is mixed, the first organic material is dissolved in the mixed solution, and the second organic material is not dissolved in the mixed solution.

20. The method as claimed in claim 19, wherein separating the purified organic material includes separating the second organic material through a filter.

21. The method as claimed in claim 12, wherein mixing the organic material with the mixed solution and purifying the organic material by stirring the mixed solution in which the organic material is mixed are performed at 20° C. to 25° C.

22. The method as claimed in claim 12, further comprising washing and drying the separated organic material after separating the purified organic material.

23. The method as claimed in claim 12, further comprising purifying and recycling the ionic liquid in the mixed solution from which the organic material is separated after separating the purified organic material.

24. The method as claimed in claim 12, further comprising preparing the mixed solution by mixing and then stirring the organic solvent and the ionic liquid prior to mixing the organic material with the mixed solution.

* * * * *

UNITED STATES PATENT AND TRADEMARK OFFICE
CERTIFICATE OF CORRECTION

| | | |
|---|---|---|
| PATENT NO. | : 10,919,007 B2 | Page 1 of 1 |
| APPLICATION NO. | : 16/144302 | |
| DATED | : February 16, 2021 | |
| INVENTOR(S) | : Myung-Ki Lee et al. | |

It is certified that error appears in the above-identified patent and that said Letters Patent is hereby corrected as shown below:

In the Claims

Column 20, Line 18, Claim 14        delete "$AlC_4^-$, $Al_2Cl_4^-$," and insert -- $AlCl_4^-$, $Al_2Cl_7^-$, --

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*